United States Patent [19]

van Staaveren

[11] Plant 4,634

[45] Jan. 27, 1981

[54] ALSTROEMERIA PLANT NAMED KING CARDINAL

[76] Inventor: M. C. van Staaveren, 30, Hornweg, 1432 GM Aalsmeer, Netherlands

[21] Appl. No.: 32,676

[22] Filed: Apr. 23, 1979

[51] Int. Cl.[3] ..... A01H 5/00

[52] U.S. Cl. ..... Plt./68

[58] Field of Search ..... Plt./68

*Primary Examiner*—Robert E. Bagwill

*Assistant Examiner*—James R. Feyrer

*Attorney, Agent, or Firm*—Chas. W. Rummler

[57] ABSTRACT

A new variety of Alstroemeria plant characterized by a profuse production of very large, deep red flowers borne on long stems, each of the successively opening flowers having 7 to 10 day lasting quality and the plant blooming recurrently first in early Spring and again in Fall.

1 Drawing Figure

BACKGROUND OF THE NEW PLANT

My new variety of red Alstroemeria originated as a seedling resulting from a cross of A. or. x 3087-3, unnamed varieties maintained by me for breeding purposes, this cross having been made by me in the course of breeding efforts carried on at Aalsmeer, Holland, in 1975 with the object of obtaining a wider color range of marketable Alstroemeria varieties. This seedling was selected for propagation because of its flower size and color and asexual reproduction was done under my direction at Aalsmeer, Holland, by dividing roots of the originial plant. Subsequent reproduction of the new plant through successive generations, again by root stock division, has shown that this Alstroemeria cultivar retains its novel and distinctive characteristics from generation to generation and these characteristics appear to be firmly fixed.

DESCRIPTION OF THE DRAWING

This new Alstroemeria cultivar is illustrated by the accompanying photographic drawing which shows the flowering characteristic of the plant as well as the flower form and coloring, the photographic print having been hand painted, in part only, to show the true colors of the flowers.

DESCRIPTION OF THE NEW PLANT

The following is a detailed description of this new variety of Alstroemeria with the color designations according to The R.H.S. Colour Chart published by The Royal Horticultural Society of London, England.

THE PLANT

Origin: Seedling.

Parentage: A. or. 6 x 3087-3, unnamed varieties maintained for breeding purposes.

Classification:

*Botanic.*—Alstroemeria.

*Commercial.*—Hybrid Alstroemeria.

Form: Erect, herbaceous bush.

Height: About 1.5 meters.

Growth: Vigorous, upright and sturdy.

Root stock: Tuberous, producing many buds during the year from which flower stalks grow in various stages of development.

Branching: Normal, each flower stalk produces 4 to 7 raceme flower bearing stems in umbel arrangement at its top.

Foliage: Quantity — abundant, with about 20 to 30 leaves.

*Leaf form.*—Long oblanceolate with acuminate apex.

*Texture.*—Soft.

*Color.*—Middle green.

THE BUD

Form: Pear shaped in beginning, becoming long pointed at time of opening.

Size: About 2.5 cm. long at opening.

Opening rate: The bud opens slowly.

Peduncle: Sturdy, extending upwardly and outwardly at an angle of about 60° from the stem.

THE FLOWER

Blooming habit: Recurrent, blooming profusely and more-or-less continuously from early Spring and in the Fall.

Size of flower: Very large.

*Diameter.*—About 5.5 to 6 cm.

*Depth.*—About 4 cm.

Borne: Singly on a long peduncle from a long and strong raceme stem.

Flower shape: Generally funnel-like.

Petalage: Number of petals — 6.

*Arrangement.*—Two concentric circles each of three petals.

*Form.*—Wide elliptic and slightly serrated at outer end.

*Texture.*—Soft.

*Appearance.*—Shiny.

*Color.*—Outer petals — 43A/B. Inner petals — body, 43A/B; base, 9A/B at opening, becoming 13A as the flower matures.

Peduncle: Long, sturdy and upright, the length depending upon the time in the growing season.

Persistence: The flowers hang on and dry.

Lasting quality:

*On plant.*—10 days.

*As a cut flower.*—7 days.

REPRODUCTIVE ORGANS

Stamens:

*Number.*—Six.

*Arrangement.*—One opposite each petal.
*Anthers.*—Length — about 7 mm.
*Filaments.*—Length — about 4 cm.
Pistils: Number — one.
*Style.*—About 3 cm. long.

This Alstroemeria cultivar is particularly distinguished by the very large size of its flowers which appear successively on long, strong, raceme stems and by the deep red coloring of its flower petals which is sharply contrasted by the bright yellow color appearing at the base of each of the inner or nectar-bearing petals. This new variety of Alstroemeria is also characterized by its vigorous growth and profuse production of flowers during a relatively long blooming season.

I claim:

1. A new and distinctive Alstroemeria cultivar, substantially as herein shown and described, characterized by the large size of its red flowers appearing on very long and strong raceme stems and by its vigorous growth and profuse flower production.

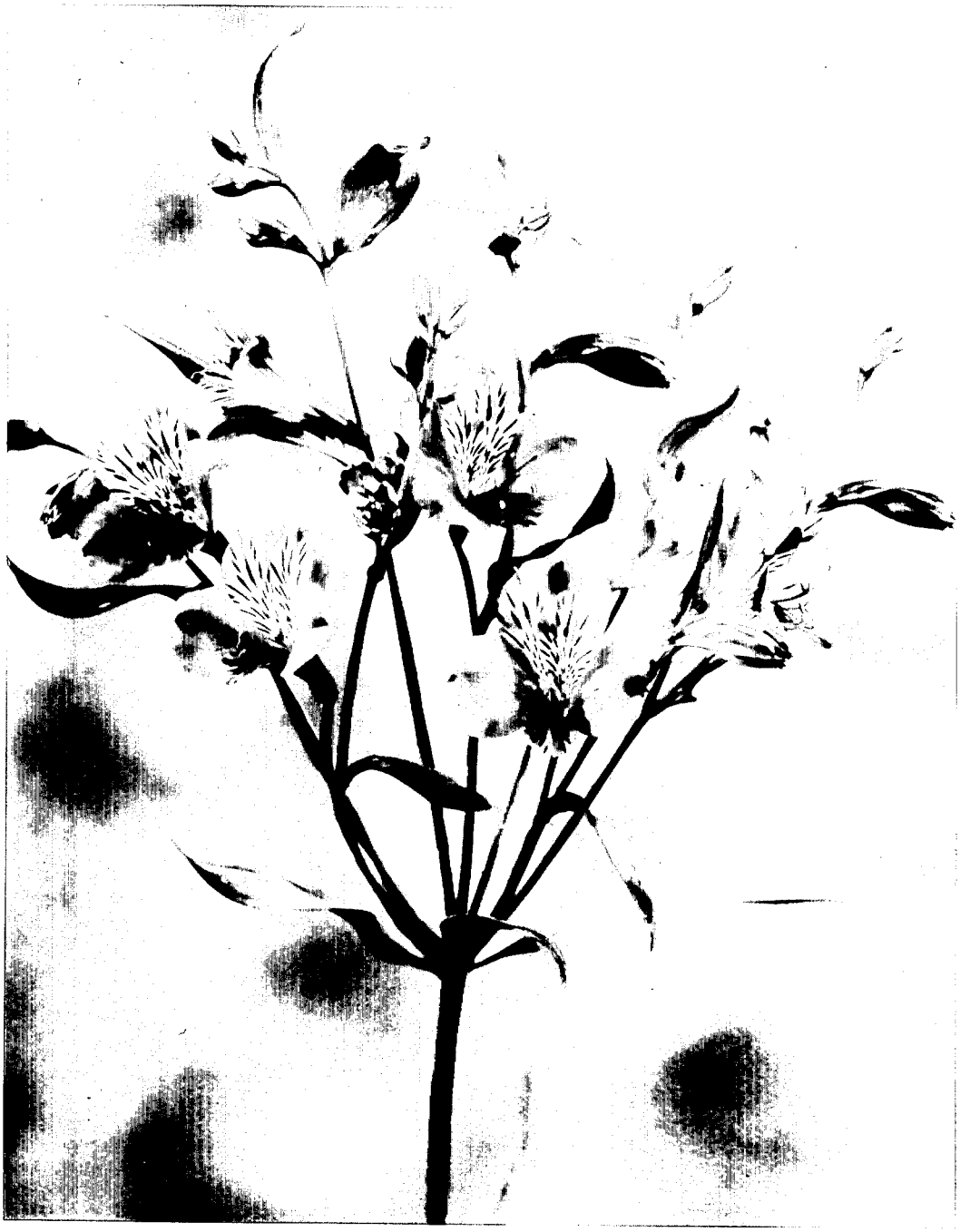

* * * * *